US006489312B1

(12) United States Patent
Stogniew et al.

(10) Patent No.: US 6,489,312 B1
(45) Date of Patent: Dec. 3, 2002

(54) PHARMACEUTICAL FORMULATIONS COMPRISING AMINOALKYL PHOSPHOROTHIOATES

(75) Inventors: Martin Stogniew, Blue Bell, PA (US); Javad M. Zadei, West Chester, PA (US)

(73) Assignee: MedImmune Oncology, Inc., West Conshohocken, PA (US)

( * ) Notice: Subject to any disclaimer, the term of this patent is extended or adjusted under 35 U.S.C. 154(b) by 0 days.

(21) Appl. No.: 09/333,411

(22) Filed: Jun. 15, 1999

(51) Int. Cl.[7] .............................................. A61K 31/66
(52) U.S. Cl. ...................................... 514/109; 514/114
(58) Field of Search ........................................ 514/109

(56) References Cited

U.S. PATENT DOCUMENTS

| | | | |
|---|---|---|---|
| 3,892,824 A | 7/1975 | Piper et al. | 260/944 |
| 4,735,210 A | 4/1988 | Goldenberg | 128/654 |
| 5,091,180 A | 2/1992 | Walker et al. | 424/944 |
| 5,112,954 A | 5/1992 | Abrams et al. | 530/391.9 |
| 5,167,947 A | 12/1992 | Geary | 424/11 |
| 5,217,964 A | 6/1993 | Edwards et al. | 514/104 |
| 5,434,145 A | 7/1995 | Edwards et al. | 514/108 |
| 5,488,042 A | 1/1996 | Grdina | 514/114 |
| 5,567,686 A | 10/1996 | Grdina | 514/43 |
| 5,605,931 A | 2/1997 | Hanson | 514/530 |
| 5,618,823 A | 4/1997 | Cavelletti et al. | 514/283 |
| 4,742,050 A | 5/1998 | Yuhas | 514/34 |
| 5,776,095 A | 7/1998 | Goldenberg | 604/20 |
| 5,846,958 A * | 12/1998 | Capizzi et al. | 414/114 |
| 5,866,591 A | 2/1999 | Gatlin et al. | 514/329 |
| 5,869,338 A | 2/1999 | Grdina | 435/375 |
| 5,891,856 A | 4/1999 | Grdina | 514/43 |
| 5,919,934 A | 7/1999 | John et al. | 546/247 |
| 5,972,986 A | 10/1999 | Seibert et al. | 514/406 |
| 6,028,114 A | 2/2000 | Quash | 514/665 |
| 6,054,622 A | 4/2000 | Zhang et al. | 568/62 |
| 6,066,688 A | 5/2000 | Hausheer | 514/492 |
| 6,075,053 A | 6/2000 | Hausheer | 514/578 |
| 6,096,399 A | 8/2000 | Ayer et al. | 424/473 |
| 6,106,866 A | 8/2000 | Ranny | 424/499 |
| 6,110,891 A | 8/2000 | Pusztai et al. | 514/8 |
| 6,114,394 A | 9/2000 | Edwards et al. | 514/646 |

FOREIGN PATENT DOCUMENTS

| | | |
|---|---|---|
| WO | WO 89/07942 | 9/1989 |
| WO | WO 99/30705 | 6/1999 |

OTHER PUBLICATIONS

Betticher et al., 1995, "Carboplatin combined with amifostine, a bone marrow protectant, in the treatment of non–small–cell lung cancer: a randomised phase II study," *Br. J. Cancer* 5:1551–1555.

Büntzel et al., 1996, "Ethyol® (Amifostine) Provides Multilineage Hematoprotection and Protection Against Non–Hematologic Toxicities Induced by Radiochemotherapy (RCT) of Head and Neck Cancer," *Blood* 88(Suppl. 1):1781.

Büntzel et al., 1996, "Selective Cytoprotection with Amifostine in Simultaneous Radiochemotherapy of Head Neck Cancer," *Annals of Oncology* 7(Suppl.5):81(381P).

Constine et al., 1986, "Protection by WR–2721 of Human Bone Marrow Function Following Irradiation," *Int. J. Radiation Oncology Biol. Phys.* 12:1505–1508.

DiPaola et al., 1996, "A Phase I Study of Amifostine and Pacliaxel in Patients with Advanced Malignancies," *Proceedings of ASCO* 15:488(1156).

Dorr et al., 1995, "Selective Cardioprotection of Rat Heart Myocytes Exposed to DNA Intercalating Agents Using Amifostine (AMI) and its Dephosphorylated Metabolite, WR–1065," *Eur. J. Cancer* 31A(Suppl. 5):S123(579).

Glover et al., 1986, "WR–2721 Protects Against the Hematologic Toxicity of Cyclophosphamide: A Controlled Phase II Trial," *J. Clin. Oncol.* 4:584–588.

Kemp et al., 1996, "Amifostine Pretreatment for Protection Against Cyclophosphamide–Induced and Cisplatin–Induced Toxicities: Results of a Randomized Control Trial in Patients with Advanced Ovarian Cancer," *J. Clin. Oncol.* 14:2101–2112.

List et al., 1996, "Amifostine Protects Primitive Hematopoietic Progenitors Against Chemotherapy Cytotoxicity," *Seminars in Oncology* 23(4)Suppl. 8:58–63.

List et al., 1996, "Amifostine Promotes Multilineage Hematopoiesis in Patients with Myelodysplastic Syndrome (MDS): Results of a Phase I/II Clinical Trial," *Blood* 88(10) Suppl 1:453a(1802) (abstract).

List et al., 1996, "Amifostine Stimulates Formation of Multipotent Progenitors and Generates Macroscopic Colonies in Normal and Myelodysplastic Bone Marrow," *Proceedings of ASCO* 15:449(1403).

Liu et al., 1992, "Use of Radiation With or Without WR–2721 in Advanced Rectal Cancer," *Cancer* 69:2820–2825.

McDonald et al., 1994, "Preliminary Results of a Pilot Study Using WR–2721 Before Fractionated Irradiation of the Head and Neck to Reduce Salivary Gland Dysfunction," *Int. J. Radiation Oncology Biol. Phys.* 29:747–754.

(List continued on next page.)

Primary Examiner—Theodore J. Criares
(74) *Attorney, Agent, or Firm*—Pennie & Edmonds LLP

(57) ABSTRACT

The present invention provides novel pharmaceutical compositions comprising aminoalkyl phosphorothioate compounds in combination with surfactants, hydrotropes and chelating agents. The compositions are well-suited for subcutaneous administration.

33 Claims, 10 Drawing Sheets

OTHER PUBLICATIONS

McDonald et al., 1995, "Amifostine Preserves the Salivary Gland Function During Irradiation of the Head and Neck," *European Journal of Cancer* 31A(Suppl. 5):415.

Nema S, et al., "Excipients and their use in injectable products", PDA J Pharm Sci Technol. 1997 Jul.–Aug.;51(4):166–71.

Phillips and Wasserman, 1984, "Promise of Radiosensitizers and Radioprotectors in the Treatment of Human Cancer," *Cancer Treat. Rep.* 68:291–302.

Reiger, M.M., 1996, *Surfactant Encyclopedia, 2nd Edition,* pp. 17–18.

Schiller et al., 1996, "Amifostine, Cisplatin, and Vinblastine in Metastatic Non–Small–Cell Lung Cancer: A Report of High Response Rates and Prolonged Survival," *J. Clin. Oncol.* 14(6):1913–1921.

Shaw et al., 1994, "Pharmacokinetics of Amifostine in Cancer Patients: Evidence for Saturable Metabolism," *Proceedings of ASCO* 13:144(371).

Shaw et al., 1988, "Pharmacokinetics of WR–2721," *Pharmac. Ther.* 39:195–201.

Shaw et al., 1986, "Human Pharmacokinetics of WR–2721," *Int. J. Radiation Oncology Biol. Phys.* 12:1501–1504.

Tabachnik et al., 1980, "Studies on the Reduction of Sputum Viscosity in Cystic Fibrosis Using and Orally Absorbed Protected Thiol," *J. Pharmacol. Exp. Ther.* 214:246–249.

Tabachnik et al., 1982, "Protein Binding of N–2–Mercaptoethyl–1,3–Diaminopropane via Mixed Disulfide Formation after Oral Administration of WR 2721," *J. Pharmacol. Exp. Ther.* 20:243–246.

Trissel LA, et al., "Compatibility of amifostine with selected drugs simulated Y–site administration", Am J Health Syst Pharm. Oct.15, 1995;52(20):2208–12.

Wadler et al., 1993, "Pilot Trial of Cisplatin, Radiation, and WR2721 in Carcinoma of the Uterine Cervix: A New York Gynecologic Oncology Group Study," *J. Clin. Oncol.* 11:1511–1516.

Wasserman et al., 1981, "Differential protection against cytotoxic chemotherapeutic effects on bone marrow CFUs by WR–2721," *Cancer Clin. Trials* 4:3–6.

Yuhas, 1973, "Radiotherapy of Experimental Lung Tumors in the Presence and Absence of a Radioprotective Drug, S–2–(3–aminopropylamino)ethylphosphorothioic Acid (WR–2721)," *J. Natl. Cancer. Inst.* 50:69–78.

NIH Publication No. 89–2141, Revised Nov. 1988.

Physicians' Desk Reference $51^{st}$ ed. (1997); pp 485–486.

Physicians' Desk Reference $52^{nd}$ ed. (1998); pp 500–502.

Physicians' Desk Reference $53^{rd}$ ed. (1999); pp 513–515.

Zadeii et al., 1991, "Stability of Ethiofos (NSC–29691) In Aqueous Solution and Solid Phase Formulation" (PDD 7184), *Pharm. Res.* 8(10):S–172.

* cited by examiner

PHARMACEUTICAL FORMULATIONS COMPRISING AMINOALKYL PHOSPHOROTHIOATES

1. FIELD OF THE INVENTION

The present invention relates to novel pharmaceutical formulations comprising aminoalkyl phosphorothioate compounds. The formulations preferably include surfactants, hydrotropes and chelating agents to, inter alia, enhance the chemical and biological properties of the aminoalkyl phosphorothioate compounds.

2. BACKGROUND OF THE INVENTION

The compound S-2-(3-aminopropylamino)ethyl dihydrogen phosphorothioate (which is also known as amifostine, ethiofos, Ethyo®, NSC 296961, and WR-2721 and which will hereinafter be referred to as "amifostine") and other aminothiol compounds are disclosed in U.S. Pat. No. 3,892,824. These compounds were originally developed as anti-radiation agents (radio-protectants), in particular to be used prior to exposure to x-ray or nuclear radiation, to protect against the harmful effects of such exposure which may be encountered during military conflicts.

In addition to its utility as a military antiradiation agent, amifostine has demonstrated excellent utility as a non-military radioprotectant and chemoprotectant, i.e., as a protectant administered prior to therapy to reduce the undesirable adverse effects which arise during the use of chemotherapy and radiation therapy in the treatment of cancer. Nygaard et al., eds, *Radioprotectors and Anticarcinogens*, Academic Press, Inc., New York, pp. 73–85 (1983); Grdina et al., *Carcinogenesis* (London) 6:929–931 (1985). In addition, these compounds have been reported to afford protection against the adverse effects of chemotherapeutic agents, for example, alkylating agents such as cisplatin, when administered before or concurrently with the chemotherapeutic agent. Jordan et al., *Exp. Mol. Pathol.* 36:297 (1982); Doz et al., *Cancer Chemother. Pharmacol.* 28:308 (1991). Similarly, it has been reported that amifostine has been used experimentally prior to therapy to protect HIV-infected patients (AIDS) from the harmful side effects of 3'-azido-3'-deoxythymidine (AZT) therapy. International Published Application WO 90/14007, published Nov. 29, 1990. Amifostine and its derivatives have been shown to exert these reported protective effects without affecting the beneficial properties of the administered therapeutic agents. This is, in the case of chemotherapy, believed to be due to the selective uptake of the protective thiol and other metabolites into normal tissue. Yuhas, *Cancer Res.* 40:1519–1524 (1980); Yuhas, *Cancer Treat. Rep.* 63:971–976 (1979).

Amifostine is indicated to reduce the cumulative renal toxicity associated with repeated administration of cisplatin in patients with advanced ovarian or non-small cell lung cancer. *Physicians' Desk Reference* $53^{rd}$ ed., p. 513–515 (1999).

Pharmaceutical compositions containing amifostine and a chelating agent to enhance gastrointestinal tract absorption of the active compound have been reported. Such compositions, suitable for oral or rectal administration, are described in U.S. Pat. No. 5,167,947. Amifostine is also being developed for subcutaneous administration. See, International Publication No. WO98/34622. In its most common use, however, amifostine is administered parenterally, including by bolus injection and intravenous infusion. Since parenteral routes circumvent the protective barriers of the human body, exceptional purity of the dosage form must be achieved. Because the dosage form must be free of microorganisms and insoluble particulates, the process used in preparing it must embody Good Manufacturing Practices ("GMP") that will produce and maintain the required quality of the product in terms of sterility and therapeutic effectiveness. Sterility is especially important in the treatment of cancer and AIDS patients, because in many instances they are already immuno-compromised and therefor highly susceptible to infections.

Amifostine has been sold as a sterile amorphous lyophilized powder containing active ingredient and mannitol. The mixture was supplied as a single use 10 ml vial containing 500 mg of amifostine and 500 mg of mannitol, and required reconstitution for intravenous infusion. *Physicians' Desk Reference*, $51^{st}$ ed. (1997) p. 485–486. Presently, a sterile crystalline dosage form of amifostine is sold under the trade name Ethyo®. *Physicians' Desk Reference*, $53^{rd}$ ed. (1999) p. 513–515. A crystal structure and preparation of a dosage form, which exhibits greater thermal stability than the previously sold amorphous dosage form, is described by U.S. Pat. Nos. 5,424,471 and 5,591,731.

Intravenous administration of amifostine suffers from several serious drawbacks. First, administering compounds intravenously is extremely inconvenient, particularly when a daily dosing schedule for several weeks, or potentially several months in the case of myelodysplastic syndrome ("MDS"), is necessary, requiring a skilled practitioner to administer the dose. Second, when administered intravenously, patients suffer from dose-dependent undesirable side-effects such as nausea, vomiting, emesis and hypotension, as well as flushing or feeling of warmth, chills or feeling of coldness, dizziness, somnolence, hiccups and sneezing. A decrease in serum calcium concentration is a known pharmacological effect of intravenously administered amifostine. Allergic reactions ranging from mild skin rashes to rigors have also rarely occurred in conjunction with intravenously administered amifostine. At present, there are no known methods, other than co-administering agents such as anti-emetics, of reducing or avoiding these undesirable side effects. Third, there are related costs associated with intravenous administration, including personnel, equipment and medical measures to attenuate side effects.

Therefore, there remains a need for pharmaceutical delivery systems which are capable of delivering amifostine and related compounds to the patient in an effective, efficient and economical manner.

3. SUMMARY OF THE INVENTION

The present invention provides novel pharmaceutical formulations comprising aminoalkyl phosphorothioate compounds. The, pharmaceutical compositions of the present invention are efficacious formulations wherein the biological and/or chemical properties of the active agent are enhanced by the addition of ingredients including, but not limited to, one or more of the following: surfactants, chelating agents and hydrotropes. These additional formulation ingredients are considered to serve, individually or in combination, inter alia, to increase the biological activity or chemical properties of the active compound.

The novel pharmaceutical formulations of the invention may be administered to a mammal, including humans, to treat or prevent a variety of disorders associated with radiation or chemotherapy, and in a manner which decreases or reduces undesirable side effects associated with the compounds. In preferred embodiments, the formulations of the invention comprise amifostine, and the formulations are administered subcutaneously.

One aspect of the invention relates to pharmaceutical formulations comprising an aminoalkyl phosphorothioate and a surfactant alone. Such formulations, in accordance with the present invention, are considered to have improved chemical and biological properties. The invention also encompasses pharmaceutical formulations comprising an aminoalkyl phosphorothioate, a surfactant and a hydrotrope, wherein the hydrotrope, inter alia, enhances the solubility of the formulation composition. The invention further encompasses pharmaceutical formulations comprising an aminoalkyl phosphorothioate, a hydrotrope and a chelating agent. The formulations of the invention having a chelating agent are considered to have enhanced biological properties. This formulation is also considered to exhibit beneficial chemical and manufacturing properties, including, inter alia, improving freeze-drying procedures and freeze-drying itself. The invention further encompasses pharmaceutical formulations comprising an aminoalkyl phosphorothioate, a surfactant, a hydrotrope, and a chelating agent.

The subcutaneous route of administration leads to a limitation in the volume of the pharmaceutical formulation used due to distention of the skin at the injection site and associated pain. Thus, the present invention has a further benefit of increasing the solubility of the active compounds in the pharmaceutical compositions of the invention, such that a greater amount of active compound can be administered per dose, without additional pain at the injection site.

Another aspect of the invention relates to sterile dosage forms of the above-described pharmaceutical compositions. The pharmaceutical compositions of the present invention may be in liquid or solid forms suitable for reconstitution such as freeze-dried or lyophilized forms, although the invention includes non-freeze-dried solids. The pharmaceutical composition may comprise a single dosage form which comprises all the components of the composition. Alternatively, the invention encompasses a dosage form kit wherein the aminoalkyl phosphorothioate compound and the remaining components of the formulation composition are provided in separate containers, and a solution for use is prepared by combining the formulation ingredients with a suitable carrier, such as sterile water prior to administration.

The pharmaceutical compositions of the invention comprising aminoalkyl phosphorothioate compounds may be adapted for administration to a patient in a number of ways, including, but not limited to parenteral (including subcutaneous, intravenous and intramuscular); or oral; mucosal (including buccal, sublingual, vaginal and rectal); topical, transdermal and the like. Subcutaneous administration is preferred.

The present invention is further directed to novel pharmaceutical compositions comprising aminoalkyl phosphorothioate and other active ingredients. Finally, the pharmaceutical compositions of the invention may also include solvents and co-solvents, excipients, antioxidants, carriers, diluents, buffers, bulking agents, solubilizers, wetting agents, suspending agents, emulsifiers and thickening agents.

4. BRIEF DESCRIPTION OF THE DRAWINGS

Figure 4A:
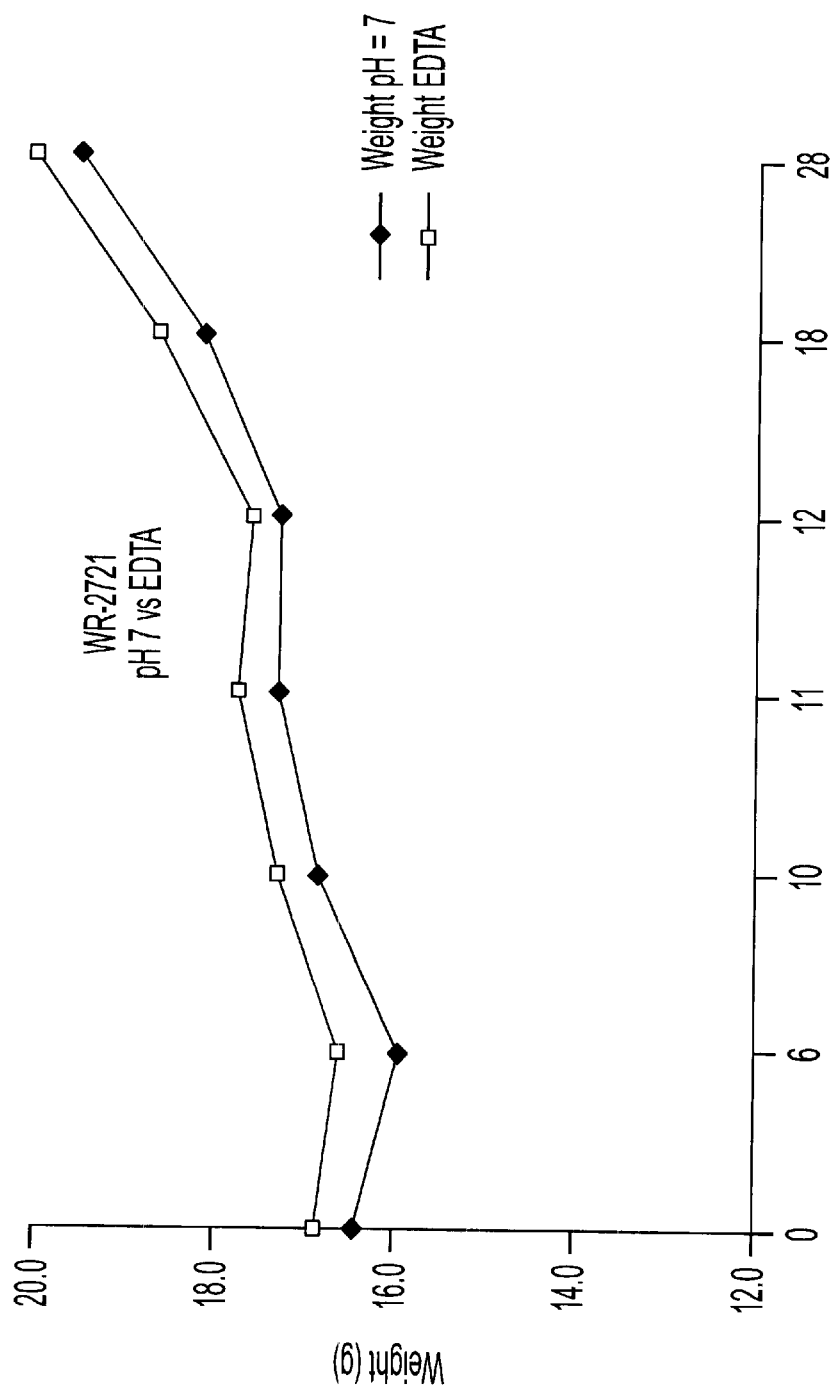
Figure 4B:
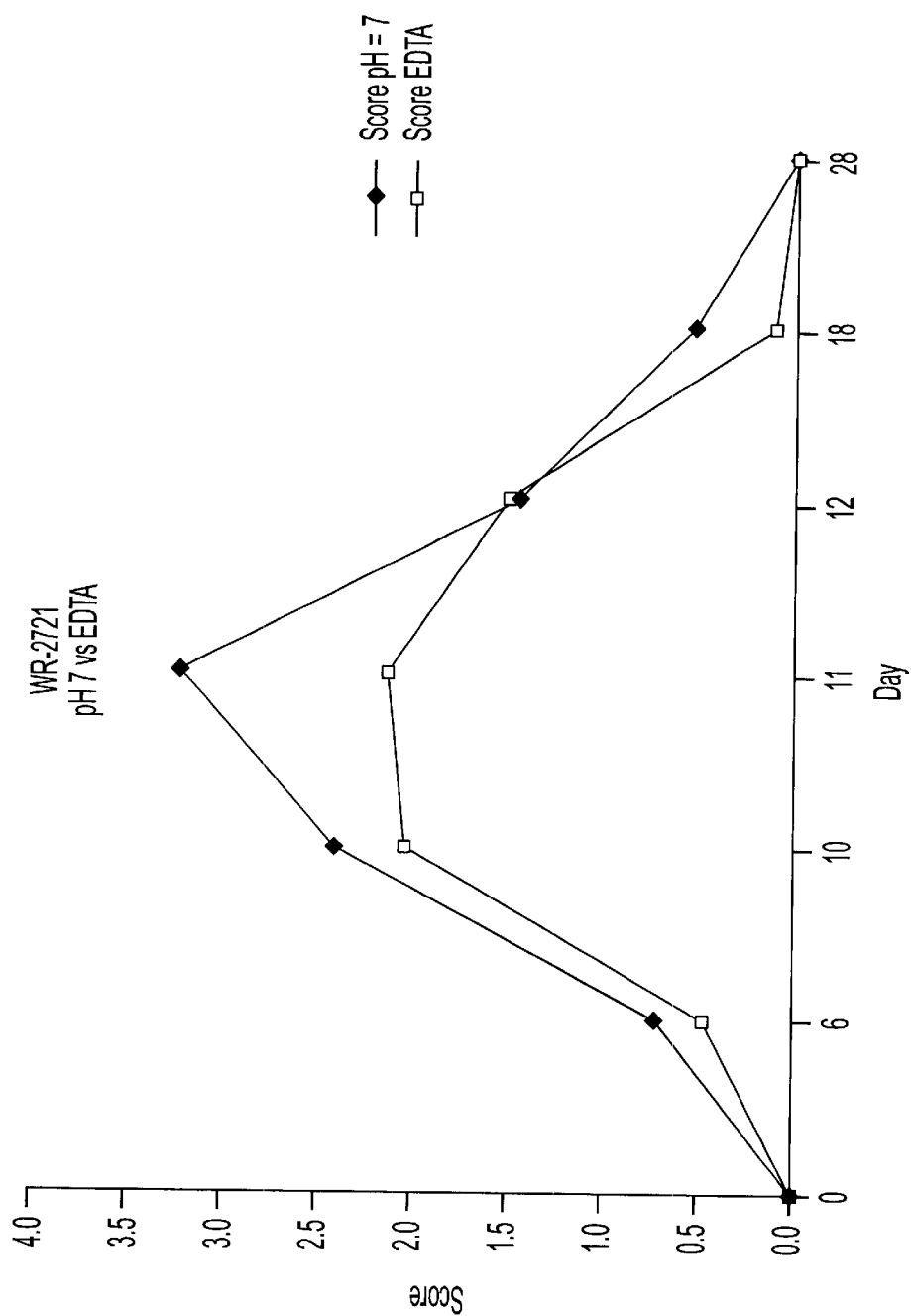

FIG. 4A is a graph comparing the weight in mice following administration of a formulation comprising 50 mg/ml amifostine and 0.2% EDTA followed by irradiation; and a formulation comprising 50 mg/ml amifostine and adjusted to pH=7 followed by irradiation. FIG. 4B compares the total mucositis scores of the formulations.

Figure 5A:
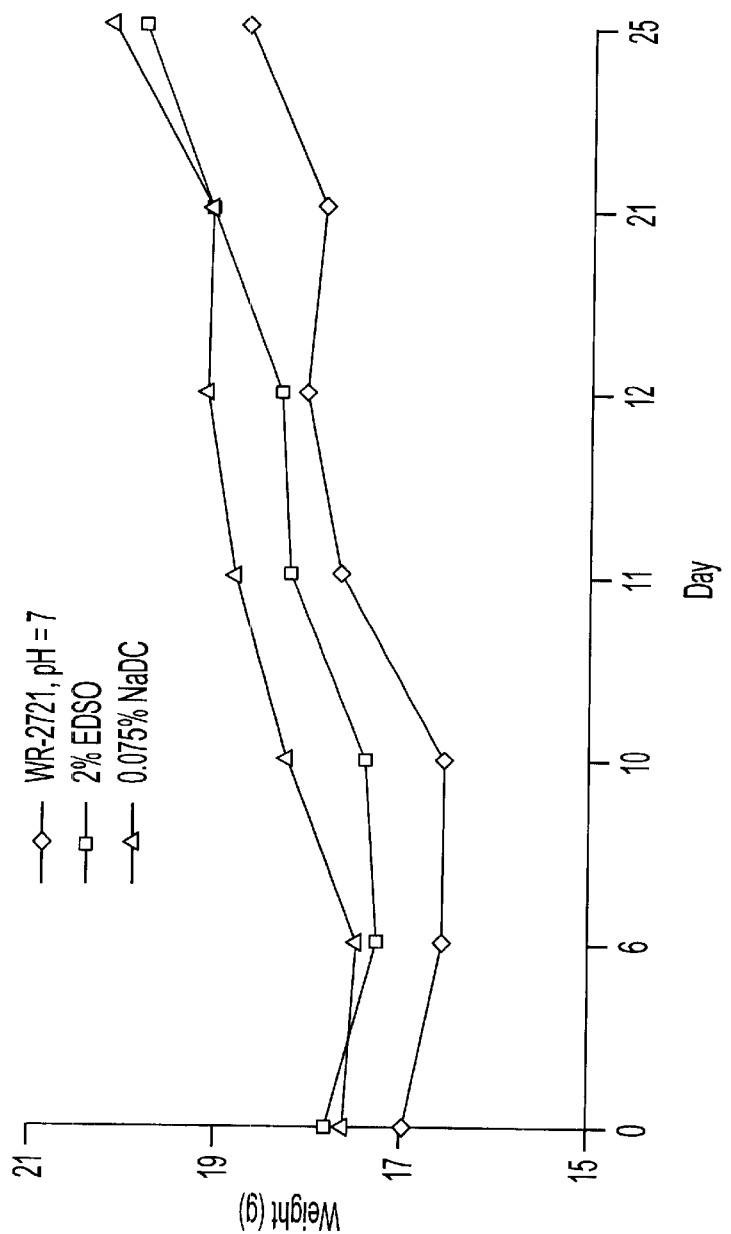
Figure 5B:
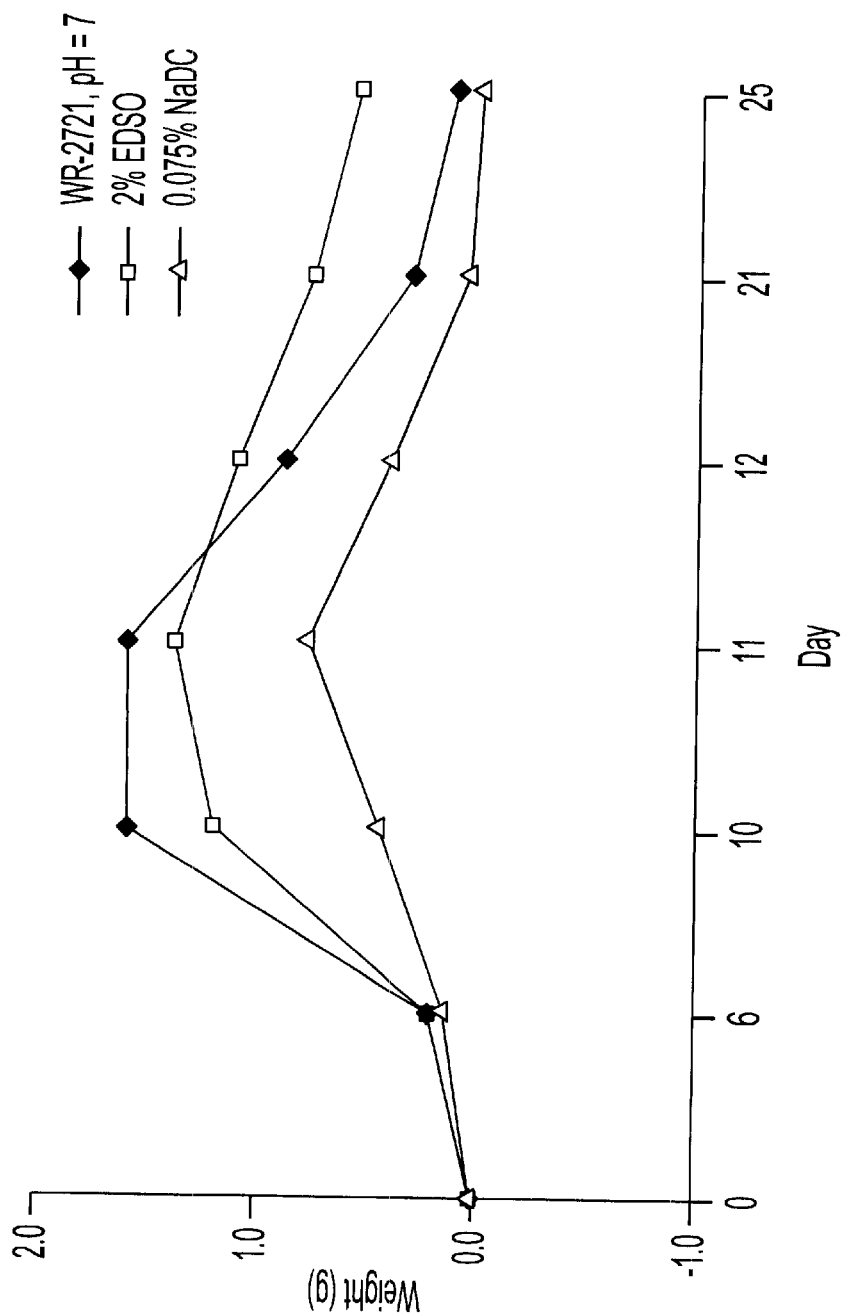

FIG. 5A is a graph comparing the weight in mice following administration of: a 50 mg/ml amifostine solution adjusted to pH=7 followed by irradiation; a formulation comprising 50 mg/ml amifostine and 0.075% sodium deoxycholate (NaDC), followed by irradiation; and a formulation comprising 50 mg/ml amifostine, 2% EDTA and 2% sorbitol (EDSO), followed by irradiation. FIG. 5B compares the total mucositis scores of the formulations.

5. DETAILED DESCRIPTION OF THE INVENTION

The present invention provides novel pharmaceutical compositions comprising aminoalkyl phosphorothioate compounds. The pharmaceutical compositions may comprise a surfactant and/or a hydrotrope and/or a chelating agent to yield a aminoalkyl phosphorothioate containing composition having enhanced chemical and biological properties. The invention is based, in part, on the surprising and unexpected discovery that the chemical, physical and/or biological properties of pharmaceutical compositions comprising aminoalkyl phosphorothioate compounds are enhanced by the addition of a surfactant and/or a hydrotrope and/or a chelating agent and/or an enzyme (such as hyaluronidase). Such enhancement can improve or facilitate the manufacture and/or use of the compositions.

While not intending to be limited by any theory, it is believed that increased biological activity may be brought about by the enhanced solubility and rate of dissolution of the active compounds in the pharmaceutical compositions. Enhanced solubility is especially desirable when the pharmaceutical composition is to be administered subcutaneously, due to the limitation on the volume of the composition which may be used. The pharmaceutical compositions of the invention may demonstrate additional beneficial properties by increasing the absorption of vitamins and other nutrients.

The formulations of the invention can be used to deliver to a mammal, including a human, the active compounds described herein. Further, the compositions are suitable for treatment or protection of patients suffering from any disorder for which the aminoalkyl phosphorothioate compounds are known or proposed to be useful. The formulations may be delivered to a patient using numerous routes of administration including, but are not limited to, inhalation, transdermal, oral, rectal, transmucosal, intestinal and parenteral administration, including intramuscular, subcutaneous, intravenous infusion or bolus injection. The preferred route of administration using the compositions of the invention is via subcutaneous administration. The formulations of the invention comprising an aminoalkyl phosphorothioate and, optionally, a surfactant and/or a hydrotrope and/or a chelating agent provide advantageous methods of treatment or protection (e.g., prevention of disease) of patients by demonstrating improved biological properties compared to formulations comprising only the active aminoalkyl phosphorothioate. These formulations are thus believed to address the need for a more efficacious dosage form for aminoalkyl phosphorothioate compounds.

The invention further provides sterile dosage forms wherein the formulation is provided in a lyophilized form, suitable for reconstitution and administration to a patient. The invention may also be provided in a form wherein the active compounds and the other ingredients of the formulation are each provided in solid non-lyophilized or lyophilized form, separate from each other. These ingredients are then reconstituted and/or solubilized in a suitable sterile liquid and combined to produce the pharmaceutical formulation, which is then suitable for administration to a patient.

The pharmaceutical compositions of the present invention comprise aminoalkyl phosphorothioate compounds in combination with a surfactant and/or a hydrotrope and/or a chelating agent, and, optionally, other ingredients. Suitable pharmaceutical ingredients are described in more detail below.

5.1 Aminoalkyl Phosphorothioates And Related Compounds

The active compounds that can be used within the formulations of the present invention include, but are not limited to, amifostine (WR-2721), as well as salts, hydrates, active metabolites, pro-drugs, and functional derivatives or analogues thereof. More specifically, the active compounds of the formulations of the invention include, but are not limited to, all pro-drugs and metabolites of amifostine and pro-drugs of the active metabolites. Thus, compounds known to the skilled artisan to be suitable for administration to humans and known to be metabolites or otherwise converted into active thiols including metabolites such as WR-1065 and WR-33278 (disulfide) and the orally bioavailable WR-151327 and its active thiols, including metabolites such as WR-151326 and its corresponding disulfide, are encompassed within the formulations.

Similarly, described herein are aminothiols that exhibit activity similar to that of amifostine or its metabolites. Preferably, these compounds are structurally related to amifostine. Alternatively, the active compounds are pro-drugs that are metabolized in vivo to a biologically active agent. Specific examples are illustrated herein.

Aminothiol compounds which can be used in the formulations of the present invention are represented by the following formula (I):

$$R_1NH(CH_2)_nNH(CH_2)_mSR_2 \qquad (I)$$

wherein $R_1$ is hydrogen, $C_5$–$C_7$ aryl, $C_2$–$C_7$ acyl, or $C_1$–$C_7$ alkyl; $R_2$ is hydrogen, $PO_3H_2$ or $R_3$, wherein $R_3$ is $R_1NH(CH_2)_nNH(CH_2)_mS$—; n and m are each an integer from 1 to 10; and preferably an integer from 2 to 6.

The formulations of the present invention also encompass the use of pharmaceutically acceptable salts and hydrates of the compounds of formula (I) above.

Preferred compounds useful in the formulations of the invention are the S-ω(ω-amino-alkylamino)alkyl dihydrogen phosphorothioate analogues represented by the formula:

$$R-NH-(C_nH_{2n})-NH-(C_mH_{2m})-S-PO_3H_2$$

wherein R is hydrogen or an alkyl group comprising 1 to 7 carbon atoms and m and n independently have a value of from 1 to 10, preferably 2 to 6.

The chemical structure of amifostine (WR-2721) can be depicted as follows:

$$H_2N-(CH_2)_3-NH-(CH_2)_2-S-PO_3H_2.$$

One preferred metabolite of amifostine is a dephosphorylated free thiol form known as WR-1065 (chemical nomenclature: S-2-(3-aminopropylamino)ethanethiol), which can be depicted as follows:

$$H_2N-(CH_2)_3-NH(CH_2)_2-SH.$$

Another preferred metabolite of amifostine is its disulfide, known as WR-33278 (chemical nomenclature: [2-[(aminopropyl)amino]ethanthiol]-N,N'-dithioidi-2,1-ethanediyl)bis-1,3-propanediamine), which can be depicted as follows:

$$H_2N-(CH_2)_3-NH-(CH_2)_2-S-S-(CH_2)_2-NH-(CH_2)_3-NH_2.$$

A preferred analogue of amifostine is the compound designated as WR-151327 (chemical nomenclature: 1-propanethiol-3-[[3-(methylamino)propyl]amino]-dihydrogen phosphorothioate), which can be depicted as follows:

$$CH_3NH(CH_2)_3NH(CH_2)_3SPO_3H_2.$$

Another preferred analogue of amifostine is the compound designated WR-151326, a dephosphorylated free thiol form of WR-151327 having the chemical structure: $CH_3NH(CH_2)_3NH(CH_2)_3SH$.

Other specific compounds suitable for use in the formulations of the present invention include, but are not limited to:

S-1-(aminoethyl)phosphorothioic acid (WR-638);
S-(2-(3-methylaminopropyl)aminoethyl]phosphorothioate acid (WR-3689);
S-2-(4-aminobutylamino)ethyl phosphorothioic acid (WR-2822);
3-[(2-mercaptoethyl)amino]propionamide p-toluenesulfonate (WR-2529);
S-1-(2-hydroxy-3-amino)propyl phosphorothioic acid (WR-77913);
2-[3-(methylamino)propylamino]ethanethiol (WR-255591);
S-2-(5-aminopentylamino)ethyl phosphorothioic acid (WR-2823);
1-[3-(3-aminopropyl)thiazolidin-2-Y1]-D-gluco-1,2,3,4,5 pentane-pentol dihydrochloride (WR-255709).

Additional aminothiols suitable for use in the formulations of the present invention include, but are not limited to, S-2-(3-ethylaminopropylamino)ethyl dihydrogen phosphorothioate, S-2-(3-aminopropylamino)-2-methylpropyl dihydrogen phosphorothioate, S-2-(2-aminoethylamino)-2-ethyl dihydrogen phosphorothioate, S-2-(4-aminobutylamino)-2-ethyl dihydrogen phosphorothioate, S-2-(5-aminopentylamino)-2-ethyl dihydrogen phosphorothioate, S-2-(6-aminohexylamino)-2-ethyl dihydrogen phosphorothioate, S-2-(2-methylaminoethylamino)-2-ethyl dihydrogen phosphorothioate, S-2-(3-methylaminopropylamino)-2-ethyl dihydrogen phosphorothioate, and S-3-(3-methylamino-propylamino)-3-propyl dihydrogen phosphorothioate (WR-151327) and pharmaceutically acceptable salts thereof. Preferably, the aminothiol is amifostine, WR-1065, WR-33278, WR-151327 or WR-151326; most preferably it is amifostine.

Amifostine, and many of its salts, analogues and derivatives thereof suitable for use in the formulations of the invention are commercially available, or can readily be prepared using standard techniques. The aminothiol compounds useful in the formulations of the invention may be prepared by methods known in the art (see, e.g., Cortese, 1943, *Organic Synthesis* pp. 91–93, Coll. Vol. II, Blatt, Ed., John Wiley & Sons, Inc., New York, N.Y.; Akerfeldt, 1960, *Acta Chem. Scand.* 14:1980; Piper et al., 1966, *Chem. Ind.* (London):2010). Certain aminothiol compounds, as well as methods of synthesizing such compounds, are described in detail in U.S. Pat. No. 3,892,824 to Piper et al., U.S. Pat. Nos. 5,424,472 and 5,591,731, both to Kennedy et al., and WO 96/25045, each of which is incorporated herein by reference in its entirety.

The aminothiol compounds useful in the formulations of the invention may be in the form of free acids, free bases, or pharmaceutically acceptable addition salts thereof. Such salts can be readily prepared by treating an aminothiol compound with an appropriate acid and/or base. Such acids include, by way of example and not limitation, inorganic acids such as hydrohalic acids (hydrochloric, hydrobromic, hydrofluoric, etc.), sulfuric acid, nitric acid, phosphoric acid, etc. and organic acids such as acetic acid, propanoic acid, 2-hydroxyacetic acid, 2-hydroxypropanoic acid, 2-oxopropanoic acid, propandioic acid, butandioic acid, etc. Conversely, the salt can be converted into the free base form by treatment with alkali.

The aminothiol compounds useful in the formulations of the invention, as well as the pharmaceutically acceptable addition salts thereof, may be in a hydrated, solvated or anhydrous form. Methods of preparing such forms will be apparent to those skilled in the art of organic chemistry.

For any mode of administration, the actual amount of active aminoalkyl phosphorothioate compound to be delivered, as well as the dosing schedule necessary will depend, in part, on such factors as the bioavailability of the active compound to be used (and/or an active metabolite thereof), the patient's condition, age and height, the disorder being treated, the desired therapeutic effect (e.g., prevention), the frequency and route of administration, and other factors that will be apparent to those of skill in the art. The actual amount delivered and dosing schedule can be readily determined by those of skill with routine experimentation by monitoring the blood plasma levels of administered compound and/or an active metabolite thereof, and adjusting the dosage or dosing schedule as necessary. Generally, between about 10 mg to about 3000 mg of active ingredient per dosage unit is used. This amount is more preferably between about 250 mg to about 1500 mg of active ingredient, and most preferably between about 400 mg to about 1000 mg of active ingredient per dosage unit.

5.2 Hydrotropes

Examples of hydrotropes which can be used within the formulations of the present invention include, but are not limited to, sorbitol, mannitol, nicotinic acid, nicotinamide, 2,5-dihydroxybenzoic acid, ascorbic acid, ascorbyl dipalmitate, fructose, glucose, glucose glutamate, glucuronic acid, glycerin, 1,2,6-hexanetriol, hydroxystearyl methylglucamine, inositol, lactose, maltitol, sorbeth-20, sucrose, thioglycerin, tris(hydroxymethyl)nitromethane, tromethamine and xylitol. A preferred group of suitable hydrotropes are polyhydroxylated alcohols. The preferred polyhydroxylated alcohol is sorbitol.

While not intending to be bound by theory, it is believed that an increase in chemical and biological properties in pharmaceutical compositions comprising an aminoalkyl phosphorothioate and a hydrotrope will be, in part, due to the enhanced solubility and rate of dissolution of aminoalkyl phosphorothioate compounds in hydrotropes. Sorbitol, a polyhydroxylated alcohol, can be utilized in pharmaceutical preparations to increase the absorption of vitamins and other nutrients. Sorbitol is approved for use as a sweetener and as a osmotic diuretic. Sorbitol is also used as a stabilizer for drug, vitamin and antacid suspensions. The present invention is based, in part, on the quite unexpected discovery that hydrotropes, including polyhydroxylated alcohols, and sorbitol in particular, enhance the solubility and rate of diffusion of aminoalkyl phosphorothioate compounds at relatively high concentrations. Hydrotropes may also be effective by enabling a selective transport of the aminoalkyl phosphorothioate compounds through tight junctions by means of passive diffusion.

The amount of hydrotrope used in the pharmaceutical compositions of the invention depends on the specific hydrotrope or blend of hydrotropes selected. However, the hydrotrope is preferably used at a concentration of from about 0.5 mg/ml to about 100 mg/ml. More preferably, the hydrotrope is used at a concentration of from about 10 mg/ml to about 30 mg/ml. Most preferably the hydrotrope is used at a concentration of about 20 mg/ml. In a preferred embodiment, the amount of hydrotrope used is such as to lead to an effective concentration of amifostine of between about 25 mg/ml and 300 mg/ml. Preferred hydrotropes include, but are not limited to nicotinic acid and nicotinamide, and polyhydroxylated alcohols such as sorbitol, mannitol and 2,5-dihydroxybenzoic acid (gentisic acid). A most preferred hydrotrope is sorbitol. In a preferred embodiment, sorbitol is used at a concentration of about 20 mg/ml.

5.3 Chelating Agents

Examples of chelating agents that can be used within the formulations of the present invention include, but are not limited to, aminotrimethylene phosphoric acid, calcium disodium ethylenediamine tetraacetic acid (EDTA), citric acid, cyclohexanediamine tetraacetic acid, diammonium citrate, diethylenetriamine pentacetic acid (DPTA), dipotassium EDTA, disodium EDTA, disodium pyrophosphate, EDTA, etidronic acid, glucuronic acid, pentapotassium triphosphate, pentasodium aminotrimethylene phosphonate, pentasodium pentetate, pentasodium triphosphate, pentetic acid, sodium citrate, sodium dihydroxyethylglycinate, sodium gluconate, sodium hexametaphosphate, sodium metaphosphate, sodium metasilicate, sodium trimetaphosphate, triethanolamine EDTA, tetrahydroxypropyl ethylenediamine, tetrapotassium pyrophosphate, tetrasodium EDTA, tetrasodium etidronate, tetrasodium pyrophosphate, tripotassium EDTA, trisodium EDTA, trisodium NTA and trisodium phosphate. Preferred chelating agents are DPTA and sodium salts of EDTA. The most preferred chelating agent is EDTA.

Chelating agents, which are also known as sequestrants, are compounds which can form stable complexes with metal ions, and thus prevent adverse effects on the stability or appearance of formulations. It was found that the chelating agents unexpectedly demonstrate the ability to enhance the biological activity of the aminoalkyl phosphorothioate compounds of the present invention.

The amount of chelating agent used in the pharmaceutical compositions of the invention depends on the specific chelating agent or blend of chelating agents selected. However, the chelating agent is preferably used at a concentration of from about 0.5 mg/ml to about 100 mg/ml. More preferably, the chelating agent is used at a concentration of from about 10 mg/ml to about 30 mg/ml. Most preferably the chelating agent is used at a concentration of 20 mg/ml. The amount of chelating agent used is such as to lead to an effective concentration of amifostine of between about 25 mg/ml and 300 mg/ml. Preferred chelating agents include, but are not limited to ethylenediamine tetraacetic acid (EDTA) and diethylenetriamine pentaacetic acid (DTPA). A most preferred chelating agent is EDTA. In a preferred embodiment, EDTA is used at a concentration of about 20 mg/ml.

5.4 Surfactants

Examples of surfactants suitable for use in the formulations of the present invention include, but are not limited to, cholic acid and salts of cholic acid, deoxycholic acid and salts of deoxycholic acid, taurocholic acid and salts of taurocholic acid, polyvinylpyrrolidone, PEG compounds such as cocamines, glyceryl stearates, glyceryl oleates, hydrogenated lanolins, lanolins, laurates and oleates, sorbitan laurates, sorbitan palmitates, sorbitan stearates, quaternium surfactants, sodium sulfates, glyceryl compounds, palmitic acid and its derivatives and oleic acid and its derivatives.

Additional suitable surfactants may be selected from the literature by one skilled in the art. (See, e.g., *Surfactant Encyclopedia* $2^{nd}$ Edition, M. M. Reiger (1996).)

A preferred subset of suitable surfactants are lipophilic surfactants. Lipophilic surfactants are surface active compounds which demonstrate an affinity for lipid compounds, which are organic waxes oils and fats, of low solubility in water but soluble in organic solvents. The surfactants of the present invention solubilize the aminoalkyl phosphorothioate compounds, thus forming a lipophilic moiety. Transcellular absorption of the aminoalkyl phosphorothioate compounds is brought about by administration of the lipophilic moiety to the patient. The invention is based, in part, on the quite unexpected discovery that pharmaceutical compositions comprising combinations of aminoalkyl phosphorothioate compounds and surfactants exhibit improved biological properties over compositions comprising only aminoalkyl phosphorothioate compounds in a suitable vehicle.

The amount of surfactant used in the pharmaceutical compositions of the invention depends on the specific surfactant or blend of surfactants selected. However, the surfactant is preferably used at a concentration of from about 0.1 mg/ml to about 10 mg/ml. More preferably, the surfactant is used at a concentration of from about 0.3 mg/ml to about 0.9 mg/ml. Most preferably the surfactant is used at a concentration of from about 0.5 mg/ml to about 0.75 mg/ml. The amount of surfactant used is such as to lead to an effective concentration of amifostine of between about 25 mg/ml and 300 mg/ml. Preferred surfactants include, but are not limited to sodium deoxycholate, sodium taurocholate TWEEN 80 and sodium dodecylsulfate. A most preferred surfactant is sodium deoxycholate. In a preferred embodiment, TWEEN 80 is used at a concentration of 1%. In another preferred embodiment, sodium dodecylsulfate is used at a concentration of 0.02%. In yet another preferred embodiment, sodium deoxycholate is used at a concentration of about 0.75 mg/ml.

Each of the above concentrations relating to the amount of hydrotrope, chelating agent and surfactant used in the formulations of the invention is calculated for a single dose composition comprising between about 10 mg to about 3000 mg of aminoalkyl phosphorothioate. This amount is more preferably between about 250 mg to about 1500 mg of aminoalkyl phosphorothioate, and most preferably between about 400 mg to about 1000 mg of aminoalkyl phosphorothioate per dosage unit.

5.5 Uses of the Pharmaceutical Compositions

The pharmaceutical compositions of the present invention can be used to efficaciously treat patients suffering from any disorder that is treatable with aminoalkyl phosphorothioate compounds.

For example, the pharmaceutical compositions of the invention can be used to selectively protect normal tissues against the toxicities associated with ionizing radiation or chemotherapy in cancer patients.

The pharmaceutical compositions of the invention comprise active compounds which are capable of stimulating bone marrow growth and causing the bone marrow function to more rapidly recover following chemotherapy. Thus, the pharmaceutical compositions of the invention further provide a useful means for administering these active compounds to patients suffering from diseases requiring bone marrow growth, such as myelodysplastic syndrome (MDS), and to patients whose bone marrow has been exposed to chemotherapy. The pharmaceutical compositions also provide a useful means for administering the active compounds to patients suffering from human immunodeficiency virus ("HIV") infection.

The preferred method of administration of the pharmaceutical compositions of the invention is by subcutaneous administration. This route of administration provides numerous advantages over other typical routes of administration, such as intravenous or bolus injection. One significant advantage is the reduction or decrease in undesirable side-effects suffered by patients receiving the therapy. Also, better patient compliance is achieved by use of subcutaneous administration, as intravenous administration is disliked by:most patients. Further, subcutaneous administration does not necessarily require administration by skilled practitioners, thus making therapy more convenient for patients.

The benefits of subcutaneous administration coupled with the benefits of the described formulations provide a unique and efficacious prevention or treatment of a variety of diseases known to be treated by amifostine.

6. Administration and Preparation of Compositions

The pharmaceutical formulations described herein, or pharmaceutically acceptable salts and/or hydrates thereof, may be administered singly, in combination with other compounds of the invention, and/or in combination with other therapeutic agents, including cancer chemotherapeutic agents. The pharmaceutical formulations may be administered alone or in an admixture with one or more pharmaceutically acceptable carriers, excipients or diluents. Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the formulations of the invention may be prepared in aqueous solutions, preferably in physiologically compatible buffers such as Hanks's solution, Ringer's solution, or physiological saline buffer. For transmucosal administration, penetrants appropriate to the barrier to be permeated are used in the formulations.

For oral administration, the formulations can be readily combined with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally comprise gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of formulation or active compound doses.

Pharmaceutical preparations which can be used orally include, but are not limited to push-fit capsules made of gelatin, as well as soft, sealed capsules made of gelatin and a plasticizer, such as glycerol or sorbitol. The push-fit capsules can comprise the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the formulations may take the form of tablets or lozenges formulated in conventional manner.

For administration by inhalation, the formulations for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated to comprise a powder mix of the formulation and a suitable powder base such as lactose or starch.

The formulations may be formulated for parenteral administration by injection, e.g., by bolus injection or continuous infusion. Formulations for injection may be presented in unit dosage form, e.g., in ampoules or in multidose containers, with an added preservative. The formulations may take such forms as suspensions, solutions or emulsions in oily or aqueous vehicles, and may comprise formulatory agents such as suspending, stabilizing and/or dispersing agents.

Pharmaceutical formulations for parenteral administration include, but are not limited to aqueous solutions of the active compounds in sterile water-soluble form. Additionally, suspensions of the pharmaceutical formulations may be prepared as appropriate oily injection suspensions. Suitable lipophilic solvents or vehicles include, but are not limited to fatty oils such as sesame oil, or synthetic fatty acid esters, such as ethyl oleate or triglycerides, or liposomes. Aqueous injection suspensions may comprise substances which increase the viscosity of the suspension, such as sodium carboxymethyl cellulose, sorbitol, or dextran. Optionally, the suspension may also comprise suitable stabilizers or agents which increase the solubility of the formulations to allow for the preparation of highly concentrated solutions.

Alternatively, the pharmaceutical formulations may be in powder form for constitution with a suitable vehicle, e.g., sterile pyrogen-free water, before use.

The pharmaceutical formulations may also be used in rectal compositions such as suppositories or retention enemas, e.g., containing conventional suppository bases such as cocoa butter or other glycerides.

In addition, the formulations may also be used as a depot preparation. Such long acting formulations may be administered by implantation (for example subcutaneously or intramuscularly) or by intramuscular injection. Thus, for example, the formulations may comprise suitable polymeric or hydrophobic materials (for example as an emulsion in an acceptable oil) or ion exchange resins, or as sparingly soluble derivatives, for example, as a sparingly soluble salt.

The pharmaceutical formulations also may comprise suitable solid or gel phase carriers or excipients. Examples of such carriers or excipients include but are not limited to, calcium carbonate, calcium phosphate, various sugars, starches, cellulose derivatives, gelatin, and polymers such as polyethylene glycols.

The formulations may be provided in a single, lyophilized dosage form, suitable for reconstitution and administration to a patient. Alternatively, the formulations may be provided in a form wherein the lyophilized aminoalkyl phosphorothioate active compounds are provided separately from the remainder of the formulation, which remainder is added to the active compound in the reconstitution step. The remainder of the formulation may be provided as a sterile aqueous solution, or in lyophilized form. The single dosage form may be prepared by loading the formulation into a vial and the vial into a freeze-drier which is than evacuated. The vial then undergoes a freeze drying, or lyophilization process which comprises freezing the composition, evacuating the lyophilization chamber and drying the frozen composition. The process may further comprise further drying using a secondary drying stage, and/or a dessicating means such as the use of dessicants, a dessicator, desiccating stoppers, and the like. Upon completion of the lyophilization, an inert gas such as nitrogen is preferably added to the vials containing the lyophilized dosage form. The dosage form wherein the aminoalkyl phosphorothioate active compounds are provided separately from the remainder of the formulation are prepared in a similar manner, with the active compounds being introduced into a vial for lyophilization, and the remainder of the formulation being introduced into a second vial for lyophilization and/or liquid fill. The formulations may further be provided in the form of a two-compartment syringe, or as a frozen solution of all the components of the composition.

6.1 Effective Dosages of Active Materials

The pharmaceutical compositions of the present invention contain the active compounds of the composition in a therapeutically effective amount, i.e., an amount effective to achieve its intended prophylactic or therapeutic purpose. Of course, the actual amount of active ingredient will depend on, among other things, its intended purpose. For example, when administered to cancer patients as a cytoprotectant in conjunction with radiation or chemotherapy, such compositions will comprise an amount of active ingredient effective to, inter alia, ameliorate the harmful effects of ionizing radiation or chemotherapeutic agents to normal tissues. When administered to patients suffering from diseases requiring bone marrow growth, such as MDS, or more rapid recovery of bone marrow function following chemotherapy, such compositions will comprise an amount of active ingredient effective to stimulate bone marrow production or function, prevent the development of or alleviate the existing symptoms of, or prolong the survival of, the patient being treated. Determination of an effective amount is well within the capabilities of those skilled in the art, especially in light of the detailed disclosure herein.

For any active compound described herein the therapeutically effective amount can be initially estimated from cell culture assays. For example, a dose can be formulated in animal models to achieve a circulating concentration range of compound, and/or an active metabolite thereof, that includes an effective concentration as determined in cell culture. Such information can be used to more accurately determine useful doses in humans. See, e.g., Washburn et al., 1976, "Prediction of the Effective Radioprotective Dose of WR-2721 in Humans Through an Interspecies Tissue Distribution Study" *Radiat. Res.* 66:100–5. Further, dosages can be extrapolated from that known for amifostine (See Physicians' Desk Reference, 1999).

Therapeutically effective amounts for use in humans can also be estimated from animal models. For example, a dose for humans can be formulated to achieve a circulating concentration found to be effective in animals.

A therapeutically effective dose can also be estimated from human pharmacokinetic data. While not intending to be bound by any particular theory, it is believed that efficacy is related to a subject's total exposure to an applied dose of administered drug, and/or an active metabolite thereof, as determined by measuring the area under the blood concentration-time curve (AUC). Thus, a dose that has an AUC of administered compound (and/or an active metabolite thereof) within about 50% of the AUC of a dose known to be effective for the indication being treated is expected to be effective. A dose that has an AUC of administered compound (and/or an active metabolite thereof) within about 70%, 80% or even 90% or more of the AUC of a known effective dose is preferred. Adjusting the dose to achieve maximal efficacy in humans based on the methods described above, particularly on the blood concentration and duration of administered compound and/or its active metabolites is well within the capabilities of the ordinarily skilled artisan.

For use as a cytoprotectant to selectively protect against the toxicities of ionizing radiation or chemotherapeutic agents, a circulating concentration of active compound of about 2 $\mu$M to 100 $\mu$M is expected to be effective, with about 5 $\mu$M to 50 $\mu$M being preferred. Alternatively, or in addition, a tissue concentration of active compound of about 4 $\mu$M to 2200 $\mu$M is expected to be effective, with about 20 $\mu$M to 350 $\mu$M being preferred.

For use as a radioprotectant against the toxicities of ionizing radiation or as a chemoprotectant against the toxicities of cancer therapy, the dose should be administered enough in advance of exposure to radiation or chemotherapy to provide effect. For i.v. administration, the dose is preferably administered within 30 min. prior to the administration of radiation or chemotherapy. For subcutaneous administration, the dose is preferably administered about 20 to 90 minutes prior to the administration of radiation therapy.

For use in treating diseases requiring bone marrow growth, such as MDS, or recovery of bone marrow function, a circulating concentration of active compound of about 2 $\mu$M to 100 $\mu$M is expected to be effective. Alternatively, or in addition, a tissue concentration of active compound of about 0.1 $\mu$M to 1000 $\mu$M is expected to be effective, with about 10 $\mu$M to 500 $\mu$M being preferred.

For subcutaneous administration of amifostine patient dosages usually range from about 50 mg/day to 1500 mg/day, commonly from about 100 mg/day to 1100 mg/day and typically from about 200 mg/day to 1000 mg/day. Stated in terms of body weight, usual dosages range from 0.5 mg/kg/day to 20 mg/kg/day, commonly from about 1.1 mg/kg/day to 18 mg/kg/day and typically from about 2.2 mg/kg/day to 16.2 mg/kg/day. Stated in terms of patient body surface areas, usual doses range from about 22 mg/m$^2$/day to 800 mg/m$^2$/day, commonly from about 45 mg/m$^2$/day to 720 mg/m$^2$/day and typically from about 90 mg/m$^2$/day to 650 mg/m$^2$/day.

7. EXAMPLE 1

Subcutaneous Administration of Amifostine Protected Animals Against Radiation-Induced Mucositis One of the major limiting acute toxicities associated with radiotherapy is radiation-induced mucositis. The ability to reduce the duration and severity of acute mucosal reactions is of particular importance in the radiotherapy and/or chemotherapy of head and neck cancer. Therefore, the radioprotective effects of amifostine were examined in an experimental model of mucositis. In particular, the study compared the radioprotective effects of amifostine by subcutaneous (s.c.) and intraperitoneal (i.p.) administration. The mouse model developed by Parkins et al. was used to examine the mucosal reactions in the inferior lip of mice after irradiation, and this model has been established as a reproducible model in the art (Parkins et al., 1983, Radiother. Oncol. 1:159–165).

7.1 Experimental Design

C57BL/6 female mice of 8-10 weeks old were used and fed with semi liquid food. The mice were randomly divided into treatment groups of five mice each. The treatment groups were, for example, Group 1: Saline solution. (s.c.) and irradiation Group 2: Amifostine, saline solution, (s.c.) and irradiation Group 3: Amifostine, 2% EDTA and 2% Sorbitol and irradiation (s.c.)

Group 4: Amifostine and 0.075% Sodium Deoxycholate and irradiation (s.c.)

Group 5: Saline solution (s.c.), no irradiation

Group 6: Amifostine and 0.2% EDTA and irradiation (s.c.)

(See also Tables below)

Unanesthetized mice were maintained in supine position and irradiated exclusively on the tip of their mouth. They were immobilized using jigs comparable to those previously used by Ang et al. (1982, Int. J. Radiat. Oncol. Biol. Phys. 8:145–148). Irradiation was performed with a RT 250 Philips apparatus delivering 1.98 Gy per min. (200 Kv, 20 mA, filter of 0.2 mm de Cu). During irradiation, a constant normobaric air renewal was maintained. The effects of amifostine were evaluated using a single dose of 16.5 Gy.

7.2 Administration of Amifostine

Amifostine was dissolved in appropriate diluent to achieve a final concentration of 50 mg/ml immediately before injections. Amifostine was dissolved in 0.075% sodium deoxycholate to achieve a final concentration of 50 mg/ml. Amifostine was dissolved in a mixture of 2% EDTA and 2% sorbitol to achieve a final concentration of 50 mg/ml. Amifostine was dissolved in 0.2% EDTA to achieve a final concentration of 50 mg/ml. Subcutaneous injections (200 mg/Kg) were conducted 30 minutes before irradiation. Where a control group was used, a first control group was injected with the saline solution and subsequently irradiated, and a second control group was injected with the saline solution, but was not irradiated.

7.3 Mucositis Scoring System

The effects of irradiation on lip mucosa were evaluated using the scoring system described by Parkins et al. (1983, Radiother. Oncol. 1:159–165). Body weight of the treated mice were scored periodically after treatment. Reduction in body weight was used as an objective indication of the severity of mucositis induced by irradiation, presumably resulting from the inability of the animals to eat. In this model, the acute reactions peaked on day 10 to 11 after irradiation.

Other symptoms of mucositis such as mucosal erythema and edema were also recorded. These symptoms developed more slowly than weight loss following irradiation. Mucosal erythema and edema were scored separately, and could be analyzed as separate scores or as a combined score yielding a maximum score of 7. Mouse lip mucosal erythema was scored according to Table 1.

TABLE 1

| Scoring System for Mucosal Erythema | |
|---|---|
| Score | Mucosal Observation |
| 0.5 | doubtful if abnormally pink |
| 1 | slight but definitely reddening |
| 2 | severe reddening |
| 3 | focal desquamation |
| 4 | exudation or crusting covering about ½ lip area |

TABLE 1-continued

| Scoring System for Mucosal Erythema | |
|---|---|
| Score | Mucosal Observation |
| 5 | exudation or crusting covering more than ½ lip area |

Mucosal edema (swelling) of the lips was scored according to table 2.

TABLE 2

| Scoring System for Mucosal Edema | |
|---|---|
| Score | Mucosal Observation |
| 0.5 | 50–50 doubtful if any swelling |
| 1 | slight but definitely swelling |
| 2 | severe swelling |

7.4 Results

Body weight reduction of irradiated mice was measured as an objective indicator of mucositis. A single dose of irradiation greatly reduced the body weight of the animals (FIG. 1). Non-irradiated animals maintained steady body weight throughout the course of the study. Less severe reductions in body weight were observed in animals which received subcutaneous injections of amifostine as compared to irradiation and saline injection.

Non-irradiated mice had no mucositis during the entire period of the experiment. In contrast, mucositis was observed in all irradiation groups.

The body weight and total mucositis score of mice following administration of a formulation comprising amifostine, compared to the body weight and total mucositis score of mice in the two control groups (one group being administered saline solution and no irradiation, the second being administered saline solution followed by irradiation) are shown in Table 3.

TABLE 3

| | Saline Solution | | Amifostine and Radiotherapy | | Saline Solution and Radiotherapy | |
|---|---|---|---|---|---|---|
| Day | Weight | Score | Weight | Score | Weight | Score |
| 0 | 16.3 | 0.0 | 16.4 | 0.0 | 16.6 | 0.0 |
| 6 | 17.0 | 0.0 | 15.8 | 0.5 | 15.7 | 1.8 |
| 10 | 17.5 | 0.0 | 17.4 | 1.7 | 13.8 | 4.6 |
| 11 | 18.2 | 0.0 | 17.8 | 1.8 | 14.8 | 5.7 |
| 12 | 18.0 | 0.0 | 17.6 | 1.3 | 15.1 | 4.6 |
| 18 | 18.7 | 0.0 | 18.4 | 0.4 | 17.5 | 3.6 |
| 28 | 19.9 | 0.0 | 19.5 | 0.0 | 19.4 | 1.6 |

Figure 1A:
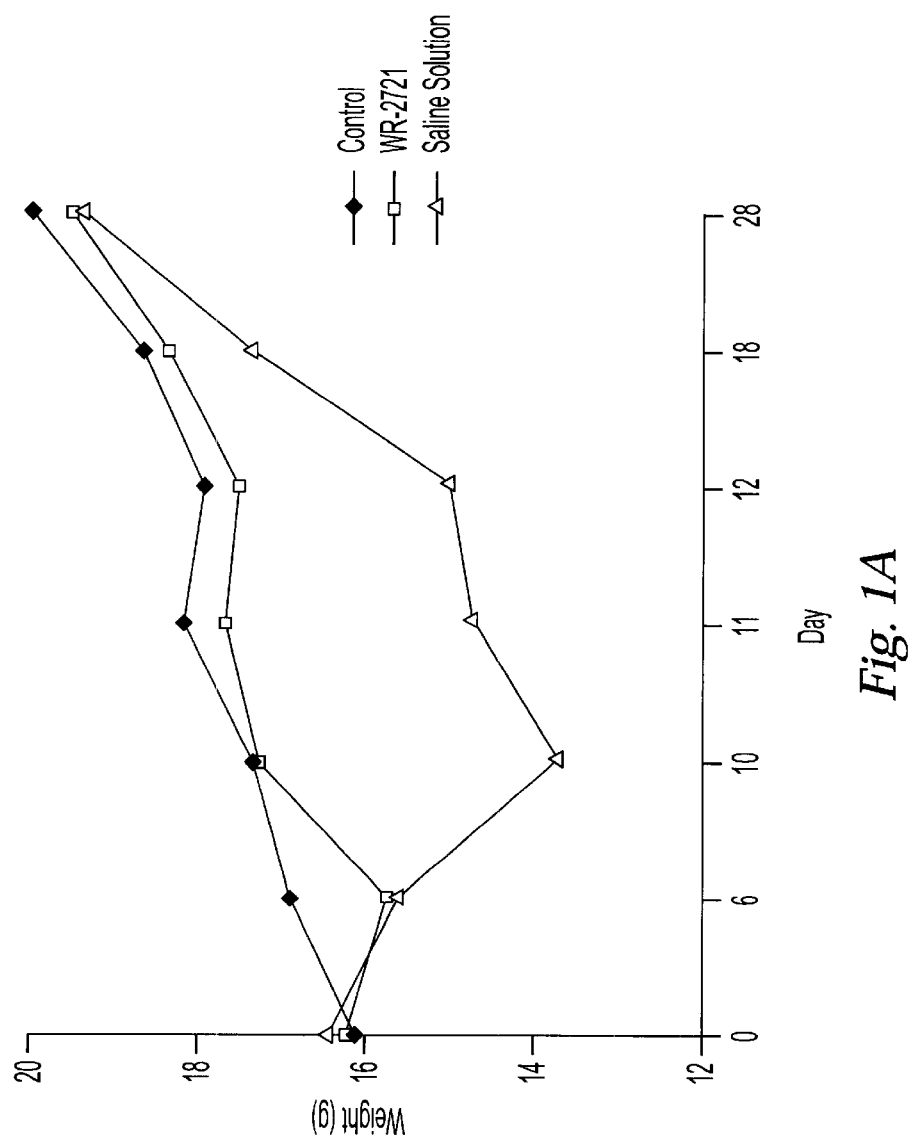
FIG. 1A is a graph comparing the weight in mice, following administration of saline solution and subsequent irradiation; 50 mg/ml amifostine solution and subsequent irradiation; and saline solution without irradiation (control).
Figure 1B:
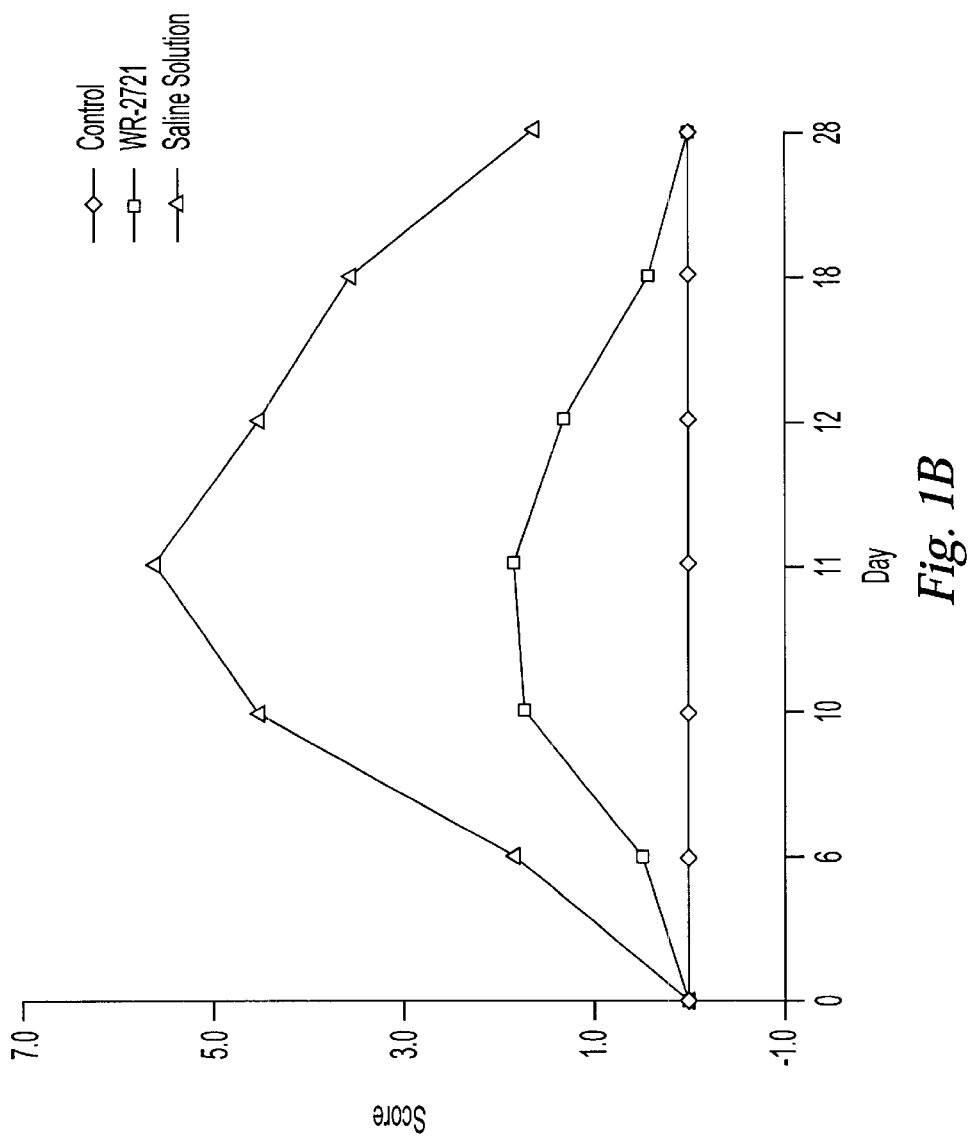
FIG. 1B compares the total mucositis scores.

The data in Table 3 are presented in graphical form in FIGS. 1A and 1B, wherein the total mucositis score and the weight change are presented.

The body weight and total mucositis score of mice receiving the formulation comprising amifostine and 0.075% sodium deoxycholate are shown in Table 4.

TABLE 4

Amifostine with 0.075% Sodium Deoxycholate

| Day | Weight | Score |
|---|---|---|
| 0 | 17.6 | 0.0 |
| 6 | 17.4 | 0.2 |
| 10 | 18.2 | 0.5 |
| 11 | 18.9 | 0.8 |
| 12 | 19.1 | 0.4 |
| 17 | 19.1 | 0.1 |
| 25 | 20.2 | 0.0 |

Figure 2A:
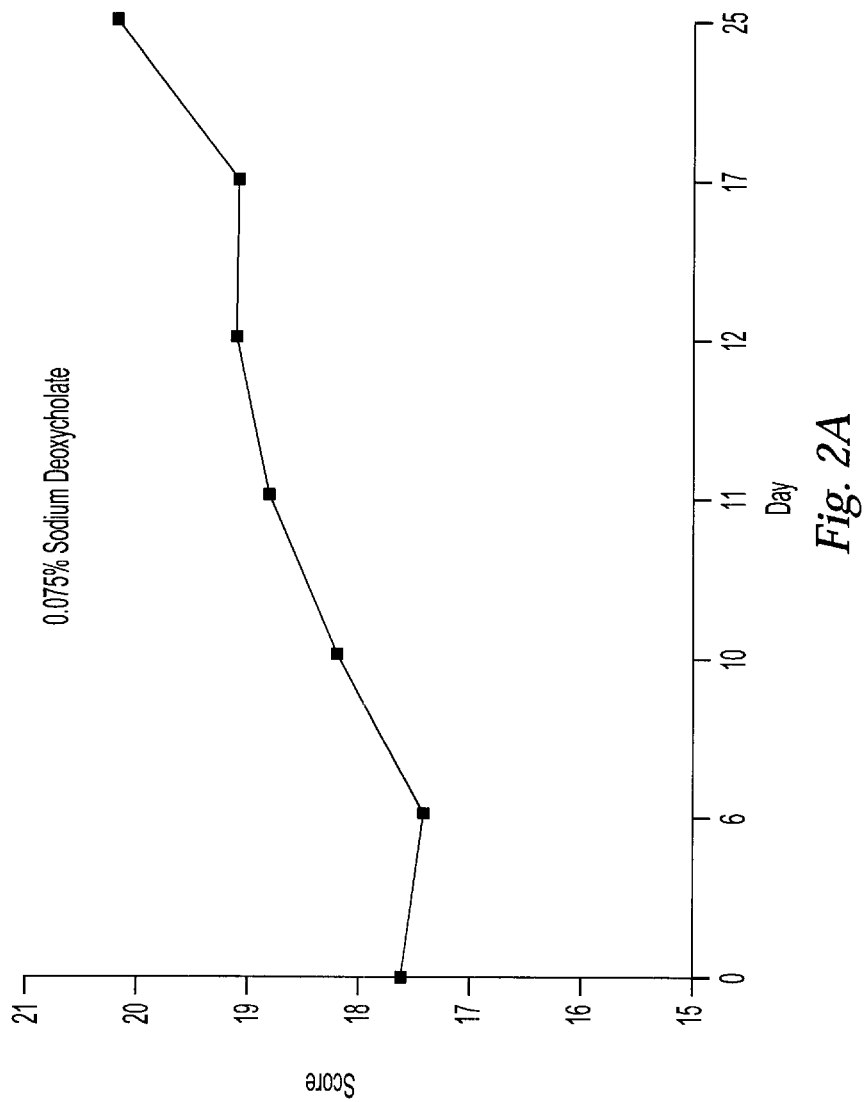
FIG. 2A is a graph of the weight in mice following administration of 50 mg/ml amifostine and 0.075% sodium deoxycholate, followed by irradiation, to 5 subjects, 0 to 25 days following irradiation.
Figure 2B:
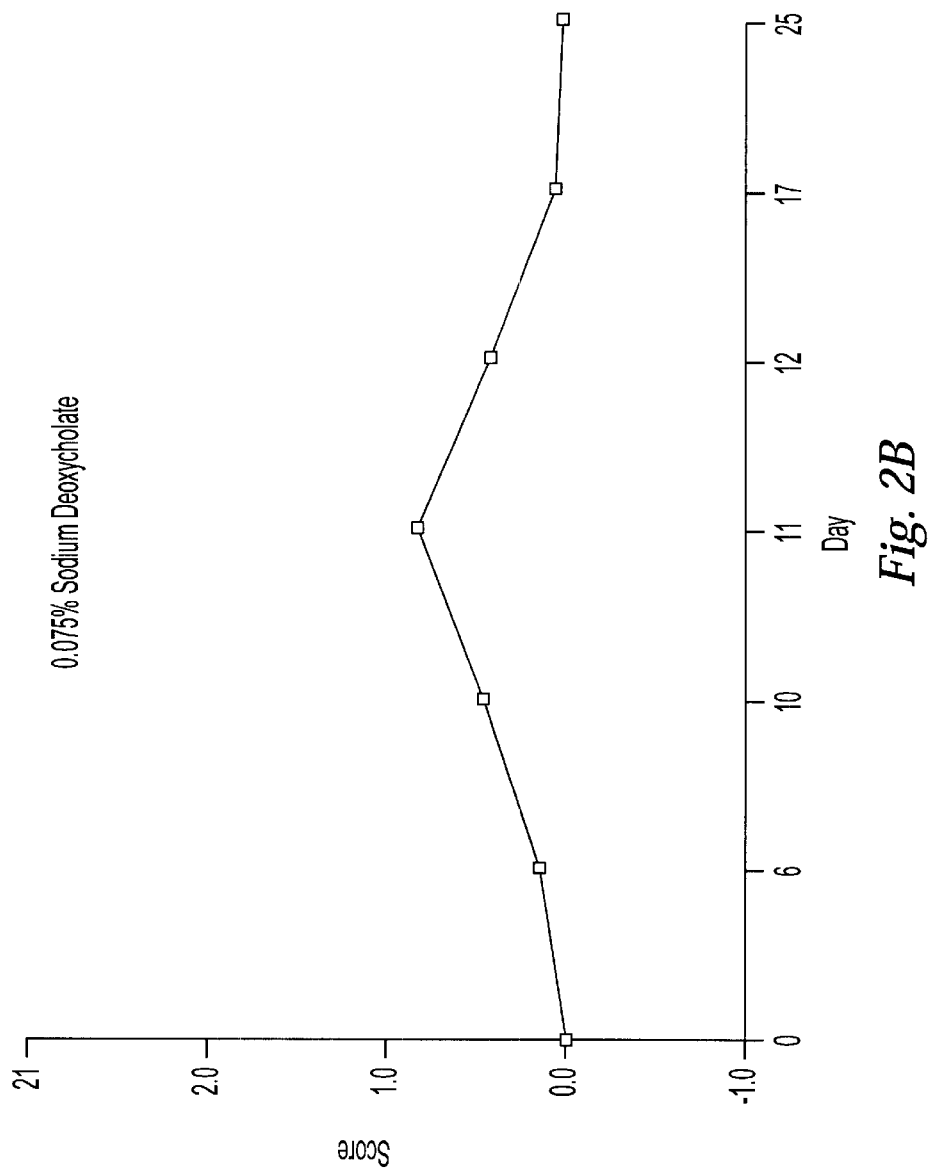
FIG. 2B depicts the total mucositis score of this formulation.

The data in Table 4 are presented in graphical form in FIGS. 2A and 2B, wherein the total mucositis score and the weight change are presented.

The body weight and total mucositis score of mice receiving the formulation comprising amifostine, 2% EDTA and 2% sorbitol are shown in Table 5.

TABLE 5

Amifostine with 2% Edetate Disodium, 2% Sorbitol; pH = 7

| Day | Weight | Score |
|---|---|---|
| 0 | 17.8 | 0.0 |
| 6 | 17.2 | 0.2 |
| 10 | 17.3 | 1.2 |
| 11 | 18.2 | 1.4 |
| 12 | 18.3 | 1.1 |
| 17 | 19.1 | 0.8 |
| 25 | 19.8 | 0.6 |

Figure 3A:
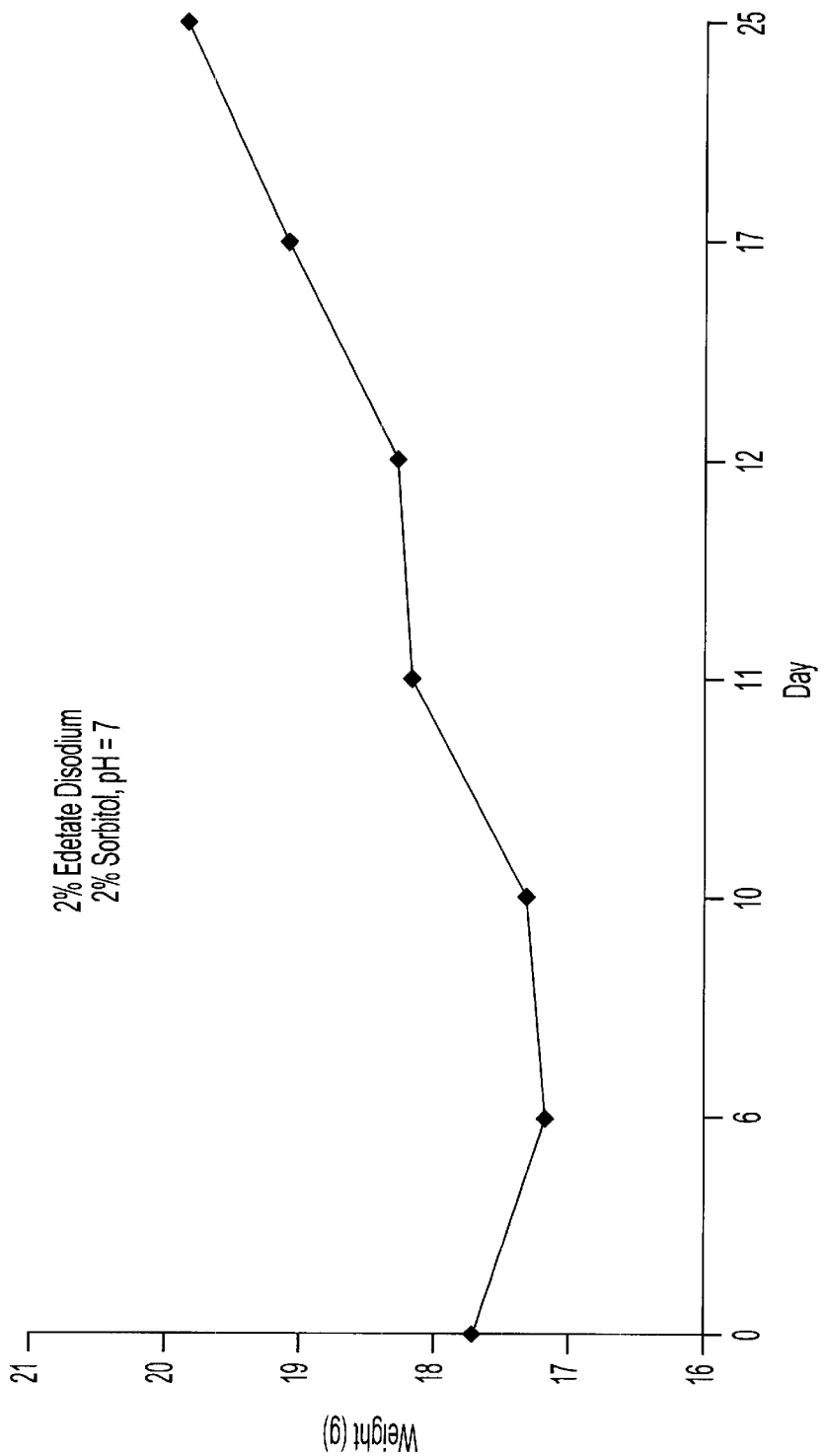
FIG. 3A is a graph of the weight in mice following administration of 50 mg/ml amifostine, 2% EDTA and 2% sorbitol, followed by irradiation, to 5 subjects, 0 to 25 days following irradiation.
Figure 3B:
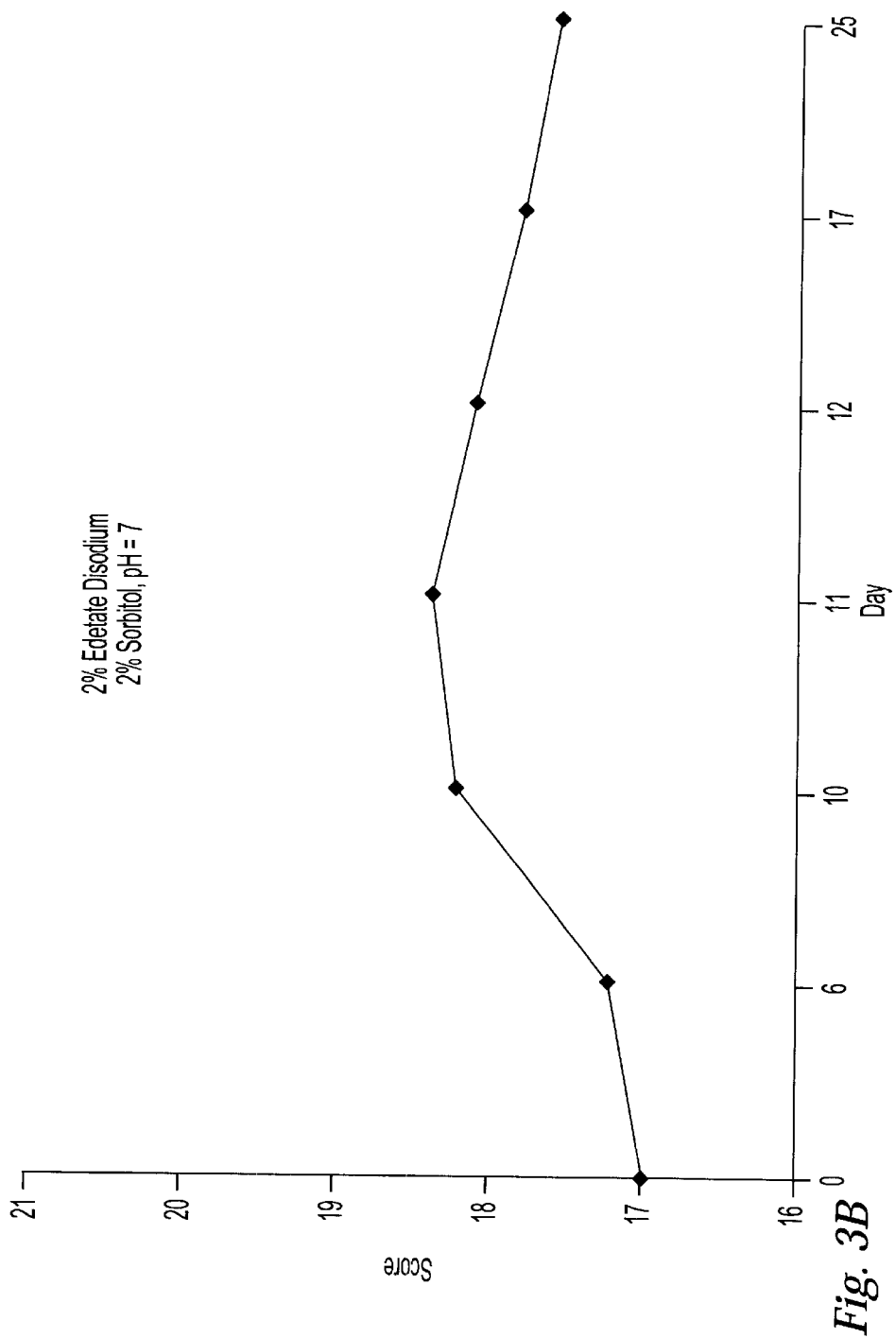
FIG. 3B depicts the total mucositis score of this formulation.

The data in Table 5 are presented in graphical form in FIG. 3, wherein the total mucositis score and the body weight are presented.

The body weight of mice following administration of a formulation comprising amifostine, compared to the body weight of mice following administration of a formulation comprising amifostine and 0.2% EDTA are shown in Table 6.

TABLE 6

| | Amifostine pH = 7 | | Amifostine with 0.2% EDTA | |
|---|---|---|---|---|
| Day | Weight | Score | Weight | Score |
| 0 | 16.5 | 0.0 | 16.9 | 0.0 |
| 6 | 16.0 | 0.7 | 16.7 | 0.5 |
| 10 | 16.9 | 2.4 | 17.3 | 2.0 |
| 11 | 17.3 | 3.2 | 17.8 | 2.1 |
| 12 | 17.3 | 1.4 | 17.6 | 1.5 |
| 18 | 18.2 | 0.5 | 18.7 | 0.1 |
| 28 | 19.5 | 0.0 | 20.0 | 0.0 |

The data in Table 6 are presented in graphical form in FIG. 4, wherein the total mucositis score and body weight of the two formulations are presented.

The body weight of mice following administration of a formulation comprising amifostine, compared to the body weight of mice following administration of a formulation comprising amifostine, 2% EDTA and 2% sorbitol, and the body weight of mice following administration of a formulation comprising amifostine and 0.075% sodium deoxycholate are shown in Table 7.

TABLE 7

| | Amifostine pH = 7 | | Amifostine with 2% Edetate Disodium 2% Sorbitol, pH = 7 | | Amifostine with 0.075% Sodium Deoxycholate | |
|---|---|---|---|---|---|---|
| Day | Weight | Score | Weight | Score | Weight | Score |
| 0 | 16.9 | 0.0 | 17.8 | 0.0 | 17.6 | 0.0 |
| 6 | 16.5 | 0.2 | 17.2 | 0.2 | 17.4 | 0.2 |
| 10 | 16.5 | 1.6 | 17.3 | 1.2 | 18.2 | 0.5 |
| 11 | 17.6 | 1.6 | 18.2 | 1.4 | 18.9 | 0.8 |
| 12 | 18.0 | 0.9 | 18.3 | 1.1 | 19.1 | 0.4 |
| 17 | 17.8 | 0.3 | 19.1 | 0.8 | 19.1 | 0.1 |
| 25 | 18.7 | 0.1 | 19.8 | 0.6 | 20.2 | 0.0 |

The data in Table 7 are presented in graphical form in FIG. 5, wherein the total mucositis score and the body weight of the formulations are presented.

The data presented in FIGS. 3, 4 and 5 show that subcutaneous administration of amifostine formulations was effective in reducing the adverse effects of radiation, as measured by the change in body weight and the visual appearance of mucositis. Furthermore, the subcutaneous administration of the formulation comprising amifostine and sodium deoxycholate produced the highest efficacy at the time point of maximal adverse effects, day 10 for body weight (FIG. 5). The formulation comprising amifostine with EDTA and sorbitol also demonstrated good protective efficacy compared to a formulation comprising amifostine alone (FIG. 5).

A comparison of the relative effects of a formulation comprising amifostine, a formulation comprising amifostine and 0.075% sodium deoxycholate, and a formulation comprising amifostine, 2% EDTA and 2% sorbitol is shown in FIG. 5. FIG. 5 clearly demonstrates the improved efficacy of the combination formulations which combine amifostine over a formulation which comprises amifostine alone.

7.5 EXAMPLE 2

These examples describe pharmaceutical formulations of the invention comprising amifostine in combination with surfactants and/or hydrotropes and/or chelating agents. The pharmaceutical formulations were administered, and the effects of irradiation on lip mucosa evaluated using the methods described in the first Example above.

TABLE 8

| Formulations With Amifostine (WR-2721) | Total Mucositis Score After 11 days | % Weight Change After 6 Days |
|---|---|---|
| Control (no radiation) | 0.0 | +5.8 |
| 0.075% Sodium Deoxycholate | 0.8 | −1.1 |
| 2% Sorbitol | 0.9 (1.8)* | −1.7 |
| 2% Edetate Disodium 2% Sorbitol, pH = 7 | 1.4 | −3.6 |
| pH = 7 | 1.6 | −2.4 |
| 2% PEG 400 | 1.7 (2.0)* | −3.6 |
| 2% Edetate Disodium 2% Sorbitol, pH = 8 | 1.9 | −2.4 |
| 2% Edetate Disodium, pH = 7 | 2.1 | 0.0 (−0.6)* |
| pH = 8 | 2.2 | −5.4 |

TABLE 8-continued

| Formulations With Amifostine (WR-2721) | Total Mucositis Score After 11 days | % Weight Change After 6 Days |
|---|---|---|
| 2% Edetate Disodium, pH = 8 | 2.5 (2.7)* | −3.0 (−3.6)* |
| pH = 8.5 | 3.1 | −4.2 (−8.3)* |
| 0.9% Saline Solution | 5.8 | −11.4 (−21.6)* |

*After 10 days

TABLE 9

| Formulations With Amifostine (WR-2721) | Total Mucositis Score After 11 days | % Weight Change After 6 Days |
|---|---|---|
| Control (no radiation) | 0.0 | +4.3 |
| 0.2% Edetate Disodium | 2.1 | −1.2 |
| pH = 8 | 2.9 | −2.4 |
| pH = 7 | 3.2 | −3.0 |
| pH = 6 | 3.2 | −5.4 |
| 1% Tween-80 | 2.4 | −4.1 |
| 1% Choline Chloride | 2.7 | −8.7 |
| 0.02% SDS | 2.4 | −11.9 |
| WR-1065 | 5.1 | −8.7 |
| 0.9% Saline Solution | 4.6 | 5.4 (−16.8)* |

*After 10 days
0.02% SDS: Sodium Dodecyl Sulfate

The most beneficial results are obtained when the mucositis evaluation score is closest to those obtained in the control group which receiving no radiation. These studies demonstrate that the best results are found in a formulation which includes amifostine and 0.075% sodium deoxycholate.

7.6 EXAMPLE 3

Dissolution Studies

The ease of dissolution of amifostine in different formulations was studied. Two sets of studies were carried out, the first using 2.2 ml of diluent to reconstitute the amifostine, the second using 2.0 ml of diluent. 500 mg of amifostine per vial was used in each study.

TABLE 10

| Amifostine with 2.2 ml of diluent | (Solubility) Reconstitution Time (Sec.) at 25° C. |
|---|---|
| 2% Sorbitol, pH = 8 | 15–20 |
| 2% Sorbitol | 15–30 |
| 2% Sorbitol, 2% EDTA Disodium, pH = 7 | 30–45 |
| 0.075% Sodium Deoxycholate | 45–60 |
| 0.05% Sodium Deoxyacholate | approx. 60 |
| Water | 45–60 |
| 0.9% NaCl | 45–60 |

TABLE 11

| Amifostine with 2.0 ml of diluent | (Solubility) Reconstitution Time (Sec.) at 25° C. |
|---|---|
| 2% Sorbitol, pH = 8 | 20–30 |
| 2% Sorbitol | 45–60 |
| 2% Sorbitol, 2% EDTA Disodium, pH = 7 | 60–75 |
| 0.075% Sodium Deoxycholate | 60–75 |
| 0.05% Sodium Deoxycholate | 90–120 |

TABLE 11-continued

| Amifostine with 2.0 ml of diluent | (Solubility) Reconstitution Time (Sec.) at 25° C. |
|---|---|
| Water | 90–120 |
| 0.9% NaCl | 90–120 |

It can be seen that the ease of dissolution of amifostine in both 2% sorbitol and a mixture of 2% sorbitol and 2% EDTA is greater than that in water.

The present invention is not to be limited in scope by the exemplified embodiments, which are intended as illustrations of individual aspects of the invention. Indeed, various modifications for the invention in addition to those shown and described herein will become apparent to those skilled in the art from the foregoing description and accompanying drawings. Such modifications are intended to fall within the scope of the appended claims.

All publications cited herein are incorporated by reference in their entireties for all purposes.

What is claimed is:

1. A pharmaceutical composition comprising a therapeutically effective amount of amifostine and sodium deoxycholate.

2. The pharmaceutical composition of claim 1, wherein the amount of amifostine is from about 10 mg to about 3000 mg.

3. The pharmaceutical composition of claim 1, wherein the amifostine is added in the form of an aqueous dispersion, said dispersion having a concentration of from about 0.1 mg/ml to about 20 mg/ml.

4. The pharmaceutical composition of claim 1, wherein the biological activity of the composition is cytoprotection, radio- or chemo-protection.

5. The pharmaceutical composition of claim 1, wherein said composition is freeze-dried or lyophilized.

6. The pharmaceutical composition of claim 1, wherein said composition is a liquid.

7. A pharmaceutical composition comprising a therapeutically effective amount of amifostine, sodium deoxycholate and a hydrotrope.

8. The pharmaceutical composition of claim 7, wherein the hydrotrope is added in the form of an aqueous solution, having a concentration of from about 0.5 mg/ml to about 100 mg/ml.

9. The pharmaceutical composition of claim 7, wherein the hydrotrope is selected from the group consisting of sorbitol, mannitol, nicotinic acid, nicotinamide, 2,5-dihydroxybenzoic acid, ascorbic acid, ascorbyl dipalmitate, fructose, glucose, glucose glutamate, glucuronic acid, glycerin, 1,2,6-hexanetriol, hydroxystearyl methylglucamine, inositol, lactose, maltitol, sorbeth-20, sucrose, thioglycerin, tris(hydroxymethyl)nitromethane, tromethamine and xylitol.

10. The pharmaceutical composition of claim 7, wherein the hydrotrope is a polyhydroxylated alcohol.

11. The pharmaceutical composition of claim 10, wherein the polyhydroxylated alcohol is sorbitol.

12. The pharmaceutical composition of claim 7, wherein said composition is freeze-dried or lyophilized.

13. The pharmaceutical composition of claim 7, wherein said composition is a liquid.

14. A pharmaceutical composition of claim 1 or 7, further comprising a chelating agent.

15. The pharmaceutical composition of claim 14, wherein the chelating agent is added in the form of an aqueous dispersion, said dispersion having a concentration of from about 0.5 mg/ml to about 100 mg/ml.

16. The pharmaceutical composition of claim 14, wherein the hydrotrope is selected from the group consisting of sorbitol, mannitol, nicotinic acid, nicotinamide, 2,5-dihydroxybenzoic acid, ascorbic acid, ascorbyl dipalmitate, fructose, glucose, glucose glutamate, glucuronic acid, glycerin, 1,2,6-hexanetriol, hydroxystearyl methylglucamine, inositol, lactose, maltitol, sorbeth-20, sucrose, thioglycerin, tris(hydroxymethyl)nitromethane, tromethamine and xylitol.

17. The pharmaceutical composition of claim 14, wherein the hydrotrope is sorbitol.

18. The pharmaceutical composition of claim 14, wherein the chelating agent is EDTA or DTPA.

19. The pharmaceutical composition of claim 14, wherein the chelating agent is EDTA.

20. The pharmaceutical composition of claim 14, wherein said composition is freeze-dried or lyophilized.

21. The pharmaceutical composition of claim 14, wherein said composition is a liquid.

22. The pharmaceutical composition of claim 14, wherein the chelating agent is EDTA.

23. A pharmaceutical composition which comprises a therapeutically effective amount of amifostine, an amount of sodium deoxycholate, an amount of sorbitol and an amount of EDTA.

24. The pharmaceutical composition of claim 1, 7, 14 or 23, wherein the composition has a pH of between about 6 and about 8.

25. The pharmaceutical composition of claim 1, 7, 14 or 23, wherein said pharmaceutical composition is adapted for use via subcutaneous administration.

26. A pharmaceutical composition adapted for use via subcutaneous administration, comprising amifostine and a compound selected from the group consisting of 0.075% Sodium Deoxycholate, 2% Sorbitol, 2% Edetate Disodium, 0.2% Edetate Disodium, 1% Tween 80, 1% Choline Chloride, 0.02% Sodium Dodecyl Sulfate, WR-1065 and mixtures thereof, and wherein the composition has a pH of between about 6 and about 8.

27. The pharmaceutical composition of claim 1, 7, 14 or 23, wherein said pharmaceutical composition is adapted for use via intravenous administration.

28. The pharmaceutical composition of claim 1, 7, 14 or 23, wherein said pharmaceutical composition is adapted for use via oral administration.

29. A unit dosage form which comprises a pharmaceutical composition of claim 1, 7, 14 or 23.

30. A method of treating a patient having cancer from the toxicities associated with radio- or chemotherapy using the pharmaceutical composition of claim 1, 7 or 14.

31. A method of protecting a patient having cancer from the toxicities associated with radio- or chemotherapy, using the pharmaceutical composition of claim 1, 7 or 14.

32. A method of treating a patient having MDS, using the pharmaceutical composition of claim 1, 7 or 14.

33. A method of protecting a patient having MDS, using the pharmaceutical composition of claim 1, 7 or 14.

* * * * *